US006879855B2

United States Patent
Schulman et al.

(10) Patent No.: US 6,879,855 B2
(45) Date of Patent: Apr. 12, 2005

(54) ZINC AIR BATTERY AND ITS USES (75) Inventors: Joseph H. Schulman, Santa Clarita, CA (US); Albert A Maltan, Stevensen, CA (US); Thomas A. Santogrossi, Chatsworth, CA (US)

(73) Assignee: The Alfred E. Mann Foundation for Scientific Research, Santa Clarita, CA (US)

( * ) Notice: Subject to any disclaimer, the term of this patent is extended or adjusted under 35 U.S.C. 154(b) by 572 days.

(21) Appl. No.: 10/117,570

(22) Filed: Apr. 5, 2002

(65) Prior Publication Data

US 2002/0110715 A1 Aug. 15, 2002

Related U.S. Application Data (63) Continuation of application No. 09/200,398, filed on Nov. 24, 1998, now abandoned.
(60) Provisional application No. 60/105,415, filed on Oct. 23, 1998.

(51) Int. Cl.$^7$ .............................. A61N 1/00; H01M 8/00
(52) U.S. Cl. ................... 607/2; 607/36; 607/55; 607/56; 607/57; 429/12; 429/27; 429/34; 429/86
(58) Field of Search .......................... 607/55, 56, 57, 607/2; 429/12, 27, 34, 86

(56) References Cited

U.S. PATENT DOCUMENTS

| | | |
|---|---|---|
| 3,871,920 A | 3/1975 | Grebier et al. |
| 3,897,267 A | 7/1975 | Tseung et al. |
| 3,963,519 A | 6/1976 | Louie |
| 4,115,626 A | 9/1978 | Sauer et al. |
| 4,364,805 A | 12/1982 | Rogers |
| 4,547,438 A | 10/1985 | McArthur et al. |
| 4,640,874 A | 2/1987 | Kelm |
| 4,693,946 A | 9/1987 | Niksa et al. |

(Continued)

FOREIGN PATENT DOCUMENTS

| | | |
|---|---|---|
| DE | 20 39 519 | 2/1972 |
| JP | 55 086073 | 6/1980 |
| JP | 59 099684 | 6/1984 |
| JP | 62 268071 | 11/1987 |
| JP | 62 274551 | 11/1987 |
| JP | 63 138668 | 6/1988 |
| JP | 07 272704 | 10/1995 |
| JP | 08 031465 | 2/1996 |
| JP | 08 106895 | 4/1996 |
| JP | 09 050828 | 2/1997 |
| WO | WO 93 12554 | 6/1993 |

OTHER PUBLICATIONS

"Clarion" CII BTE Behind–the–Ear–Processor 2001 Advanced Bionics Corporation.

"Platinum Series Behind–the–Ear–Processor", 2000 Advanced Bionics Corporation.

"Duracell Becomes First Licensee of AER Energy Zinc–Air Technology", AER Energy Resources, Inc. 1998.

Duracell Zinc Air, pp. 1–15.

Primary Examiner—Kennedy Schaetzle
Assistant Examiner—Alyssa M. Alter
(74) Attorney, Agent, or Firm—Lee J. Mandell (57) ABSTRACT

The invention is a method for increasing the airflow to a zinc-air battery such that the energy density is 500 mwh/cc to 1000 mwh/cc. This allows 8 to 16 hours use as a primary (throw-away) battery, with, for example, high-duty cycle, high-drain cochlear implants, and neuromuscular stimulators for nerves, muscles, and both nerves and muscles together. The systems incorporating the high energy density source are also part of the invention, as well as the resulting apparatus of the method. The uses of this inexpensive, i.e., a $1.00 per day, throw-away primary battery are new uses of the modified zinc-air battery and are directed toward helping people hear again, walk again, and regain body functionality which they have otherwise lost permanently.

20 Claims, 9 Drawing Sheets

U.S. PATENT DOCUMENTS

| | | |
|---|---|---|
| 4,756,980 A | 7/1988 | Niksa et al. |
| 4,842,963 A | 6/1989 | Ross, Jr. |
| 4,894,295 A | 1/1990 | Cheiky |
| 5,187,746 A | 2/1993 | Narisawa |
| 5,191,274 A | 3/1993 | Lloyd et al. |
| 5,240,785 A | 8/1993 | Okamura et al. |
| 5,249,234 A | 9/1993 | Butler |
| 5,306,578 A | 4/1994 | Ohashi et al. |
| 5,328,777 A | 7/1994 | Bentz et al. |
| 5,328,778 A * | 7/1994 | Woodruff et al. ............. 429/27 |
| 5,451,473 A | 9/1995 | Oltman et al. |
| 5,458,988 A | 10/1995 | Putt |
| 5,506,067 A | 4/1996 | Tinker |
| 5,522,865 A | 6/1996 | Schulman et al. |
| 5,531,774 A | 7/1996 | Schulman et al. |
| 5,549,658 A | 8/1996 | Shannon et al. |
| 5,554,452 A | 9/1996 | Delmolino et al. |
| 5,569,307 A | 10/1996 | Schulman et al. |
| 5,569,551 A | 10/1996 | Pedicini et al. |
| 5,571,148 A | 11/1996 | Loeb et al. |
| 5,571,630 A | 11/1996 | Cheiky |
| 5,584,869 A | 12/1996 | Heck et al. |
| 5,601,617 A | 2/1997 | Loeb et al. |
| 5,603,726 A | 2/1997 | Schulman et al. |
| 5,609,616 A | 3/1997 | Schulman et al. |
| 5,652,068 A | 7/1997 | Shuster et al. |
| 5,665,481 A | 9/1997 | Shuster et al. |
| 5,721,064 A | 2/1998 | Pedicini et al. |
| 5,724,431 A | 3/1998 | Reiter et al. |
| 5,776,172 A | 7/1998 | Schulman et al. |
| 5,824,022 A | 10/1998 | Zilberman et al. |
| 5,876,425 A | 3/1999 | Gord et al. |
| 5,938,691 A | 8/1999 | Schulman et al. |
| 5,948,006 A | 9/1999 | Mann |
| 6,051,017 A | 4/2000 | Loeb et al. |
| 6,052,624 A | 4/2000 | Mann |
| 6,067,474 A | 5/2000 | Schulman et al. |
| 6,164,284 A | 12/2000 | Schulman et al. |
| 6,175,764 B1 | 1/2001 | Loeb et al. |
| 6,181,965 B1 | 1/2001 | Loeb et al. |
| 6,185,452 B1 | 2/2001 | Schulman et al. |
| 6,185,455 B1 | 2/2001 | Loeb et al. |
| 6,195,585 B1 | 2/2001 | Karunasiri et al. |
| 6,208,894 B1 | 3/2001 | Schulman et al. |
| 6,240,316 B1 | 5/2001 | Richmond et al. |
| 6,272,382 B1 | 8/2001 | Faltys et al. |
| 6,275,737 B1 | 8/2001 | Mann |

* cited by examiner

ZINC AIR BATTERY AND ITS USES

This application is a continuation of U.S. patent application Ser. No. 09/200,398, filed Nov. 24, 1998, now abandoned, which claims benefit of Provisional Ser. No. 60/105,415, filed Oct. 23, 1998.

FIELD OF THE INVENTION

The invention relates to the fields of portable high-density energy sources and small batteries capable of high power rates. It also relates to cochlear implant systems and to functional electric stimulation (FES), electric stimulators and to muscle and nerve stimulators (neuromuscular stimulators).

BACKGROUND OF THE INVENTION

Certain types of biological tissue stimulators, such as heart pacemakers, have a low duty cycle, and draw relatively little power over the course of some time frame, say, an hour. On the other hand, other biological stimulator types have a higher duty cycle, and may thus draw relatively higher power. Such higher power stimulators include, for example, a class of cochlear implants, as well as electrical stimulators for muscles and for nerves, such as in the case of stimulators for muscles which have their nerves inoperative because of trauma or degenerative illnesses, or, for nerves which may not be receiving normal synaptic input from the other ordinarily incoming other nerves, because of loss or disconnection (i.e., severing of those other nerves). For example, the spinal column nerves may be severed at some point, and the restoration of function below the cut area may be enabled with high-powered electric stimulators. These functions may include lower gastrointestinal (GI) function, urinary functions, sexual functions, and walking and limb movement functions, all of which may be served by functional electrical stimulators (FES) or other neuromuscular stimulators.

Today's primary battery sources tend to be of not high enough energy density, or if high enough energy density, too expensive and too large for any real use as a primary battery for any of the uses and systems above. Consequently, there is a real, unmet need for such systems, and such a power unit. A high amount of energy stored in a small space is a high energy density apparatus. Such an apparatus can potentially supply a high amount of energy per unit time (power) before it is exhausted. The current teaching of the art is away from this high energy density, relatively cheap, primary battery and systems which utilize it, and toward small, relatively low energy density, rechargeable batteries.

SUMMARY OF THE INVENTION

The present invention addresses the above and other needs by providing a primary battery for use in the systems above that is prismatic in shape, small in size, and inexpensive to make.

In accordance with one aspect, the invention provides a method for increasing the airflow to a zinc-air battery such that the energy density is 500 mwh/cc to 1000 mwh/cc. This thereby allows the battery to be used for approximately 8 to 16 hours as a primary (throwaway) battery, with, for example, high-duty cycle, high-drain cochlear implants, and neuromuscular stimulators for nerves, muscles, and for nerves and muscles together.

In accordance with another aspect of the invention, there are provided medical stimulation systems and methods incorporating a high energy density source, e.g., a zinc-air battery having increased airflow. Therefore, advantageously, due to the small prismatic shape and small size of the power source, such systems can be housed in a much more compact and useful space than has heretofore been possible. Moreover, due to the cost of the power source, it represents an inexpensive, i.e., a $1.00 per day, throw-away primary battery that may be used in systems directed toward helping people hear again, walk again, and regain body functionality which they may have otherwise lost permanently.

One embodiment of the invention may be characterized as a small high energy density battery having a rectangular solid shape with dimensions of approximately 8 mm thick by 20 mm long by 17 mm wide. Such a small prismatic shape allows it to fit slidingly into a behind-the-ear external speech-processing component of a cochlear implant system. Hence, while existing cochlear implants systems use belt-mounted batteries and speech processors, the system of the present invention with its new high-density energy source allows the belt-mounted batteries and speech processor to be dispensed with and to be replaced by a lightweight behind-the-ear (BTE) unit.

The casing of the high energy density source includes a non-reactive plastic or other non-reactive material, which contains small holes in it. Or it is in part, or, whole, permeable to air allowing a sufficient flow of air to enter so that the air may react with the zinc in the zinc-air battery configuration to produce the desired power. A characteristic feature of a zinc-air battery is that the energy produced by the battery results from a reaction between the oxygen in the air and zinc. Moreover the amount of energy produced is, in large part, a function of how much air is flowing to the air electrode part of the battery.

Smaller "button" batteries of the zinc-air type disadvantageously have high series equivalent impedance. In order to get a higher current and power and lower impedance from this battery type, a larger size is needed. Prior teaching is toward a small size because the amount of air required for a smaller battery is more easily accomplished, while the casing of a larger battery makes it impossible to supply the required air. The present invention advantageously overcomes these difficulties and provides a lower impedance battery in a small prismatic package having higher energy density than has been heretofore achieved.

Thus, with the invention herein, a whole new area is opened up for neuromuscular electric stimulation, as well as for cochlear implants, requiring a small, high energy-density source.

BRIEF DESCRIPTION OF THE DRAWINGS

The above and other features and advantages of the invention will be more apparent from the following detailed description wherein.

DETAILED DESCRIPTION OF THE PREFERRED EMBODIMENTS

The following description is of the best mode presently contemplated for carrying out the invention. This description is not to be taken in a limiting sense, but is merely made for the purpose of describing the general principles of the invention. The scope of the invention should be determined with reference to the claims.

Figure 1A:
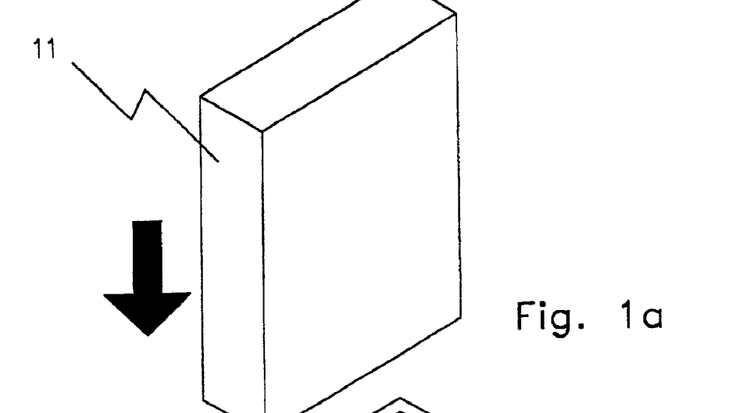
FIG. 1a is a high energy density primary zinc-air battery with permeable casing.
Figure 1B:
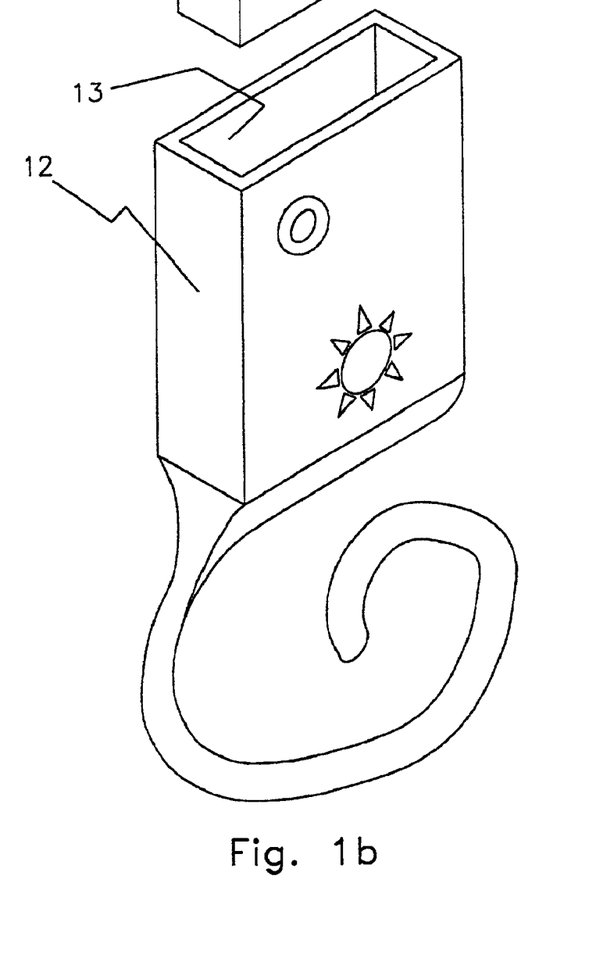
FIG. 1b shows a Behind-The-Ear (BTE) cochlear implant component with battery receiving chamber.
Figures 1C, 1D:
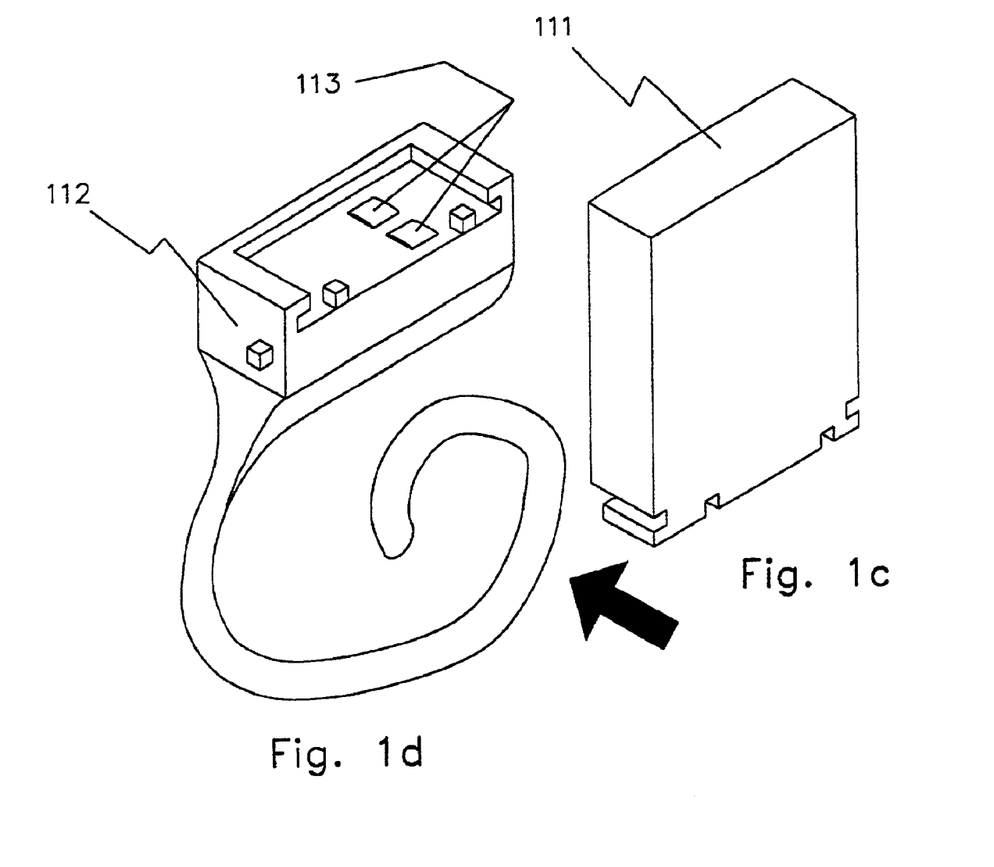
FIG. 1c shows a different embodiment of is a high energy density primary zinc-air battery with permeable casing.
FIG. 1d shows another embodiment of the BTE cochlear implant component with a variant battery holding unit.
Figures 1E, 1F:
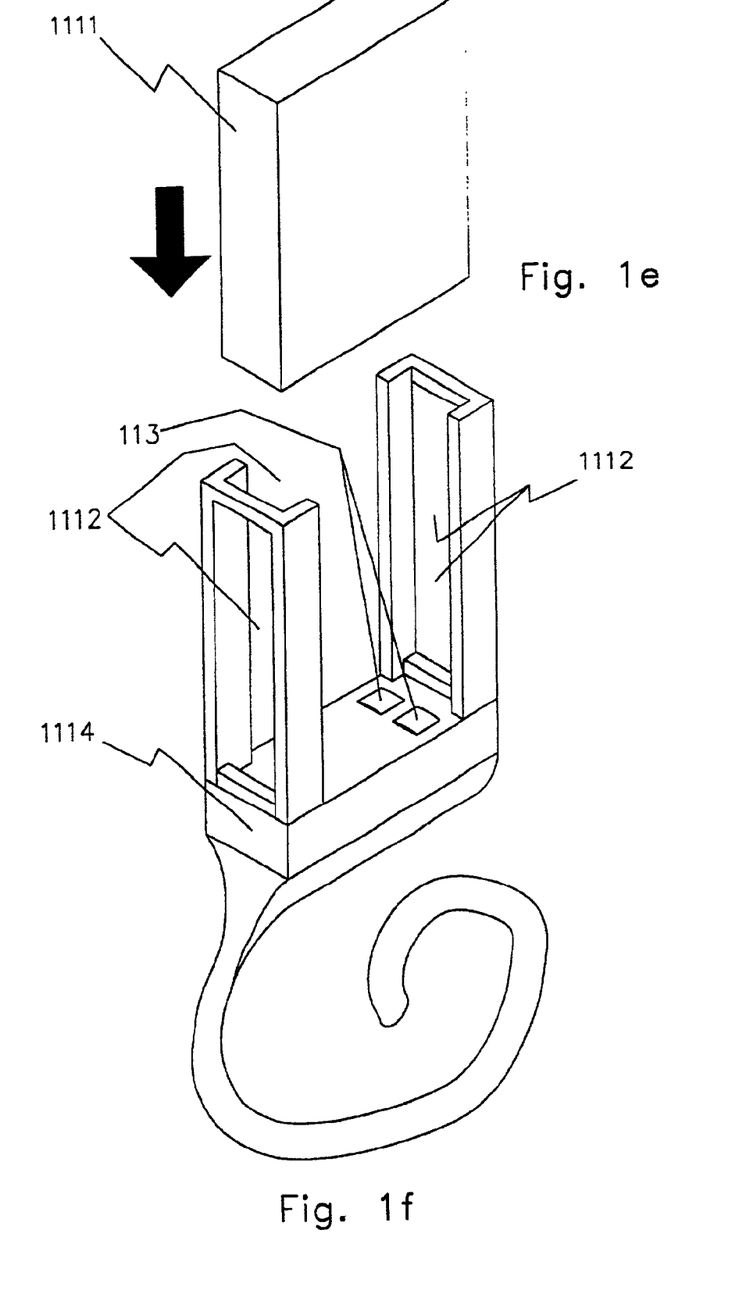
FIG. 1e shows a different embodiment of a high energy density primary zinc-air battery with permeable casing.
FIG. 1f shows another embodiment of the BTE cochlear implant component with a different variant battery holding unit.

As in FIG. 1a, the zinc-air battery (11) may be slid into a battery receptacle (13), for example, as in FIG. 1b, of a behind-the-ear unit of a cochlear implant system (12). As shown in FIG. 1c, in another embodiment, the zinc-air battery (111) slides into the battery holder of the BTE (112) part of the cochlear implant system, as in FIG. 1d. The electrical contacts (113) of the BTE (112) unit mate by simple spring pressure to the corresponding contact points on the zinc-air battery (111), which are not shown. A third embodiment is shown in FIG. 1e, with the zinc-air battery (1111) slidingly mating with the BTE battery holding case (1114) as shown in FIG. 1f. The battery case (1114) has large air openings (1112) as well as spring loaded electrical contacts (113) which contact corresponding electrical contacts on the battery (1111).

The zinc-air battery uses the oxygen from the air as one electrode and a consumable metal, zinc, as the other electrode. The electrochemical reaction is mediated by a suitable electrolyte. A principal advantage of the zinc-air battery is that the weight and volume of the battery are cut way down, because one electrode is consumable, ambient air, and an amount of a second metal corresponding to that of the first electrode need not be included. However, to get the air to the electrochemical reaction, provision for the air to come into the battery, e.g., holes, permeable membranes, and airways or such, need to be provided.

In the range of zinc-air battery weight, size, and power considered for the present invention, more provision for air entry is required than in a simple button battery. That is, a simple hole will not suffice to provide the necessary air transport. On the other hand, an air management system with fans, and possibly coolers and heaters and active desiccator (s) and/or humidifier(s), would be prohibitive in expense, size, and weight for the batteries in the present invention, but would be suitable for the ease of some larger zinc-air batteries.

Figure 2A:
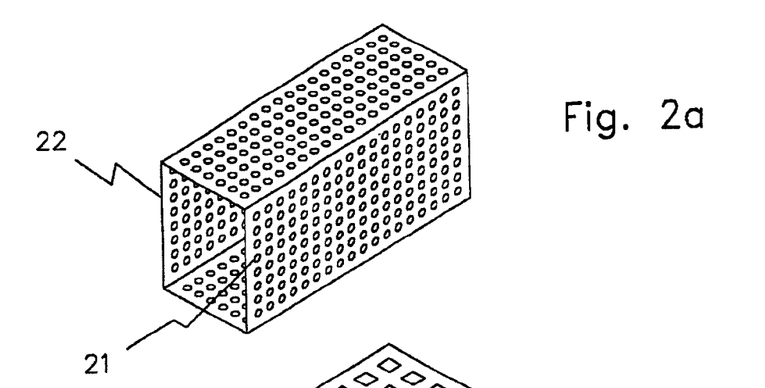
FIG. 2a shows a permeable casing that utilizes small holes.
Figure 3A:
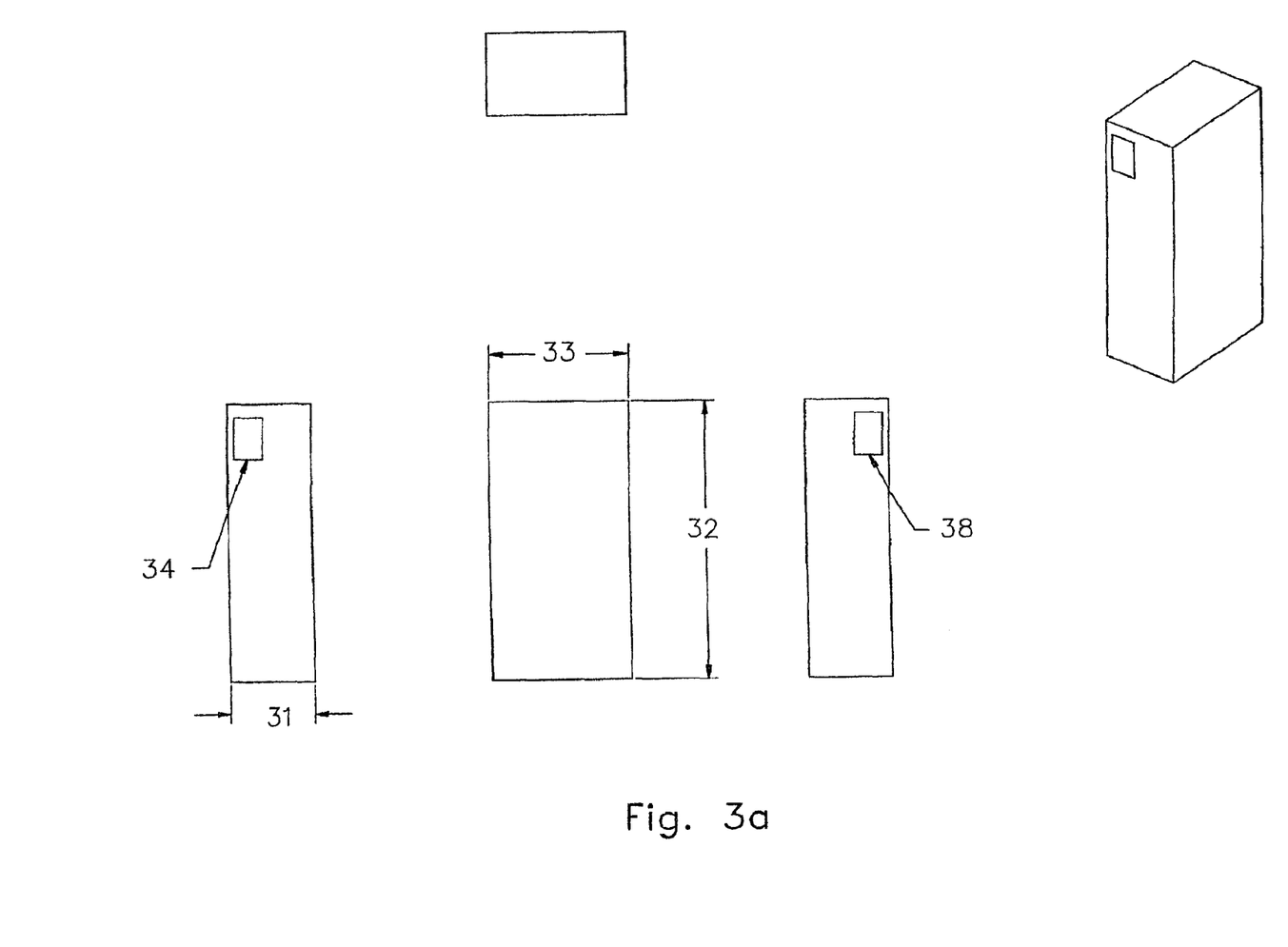
FIG. 3a shows the range of dimensions of a zinc-air battery for use in cochlear implant systems.
Figure 3B:
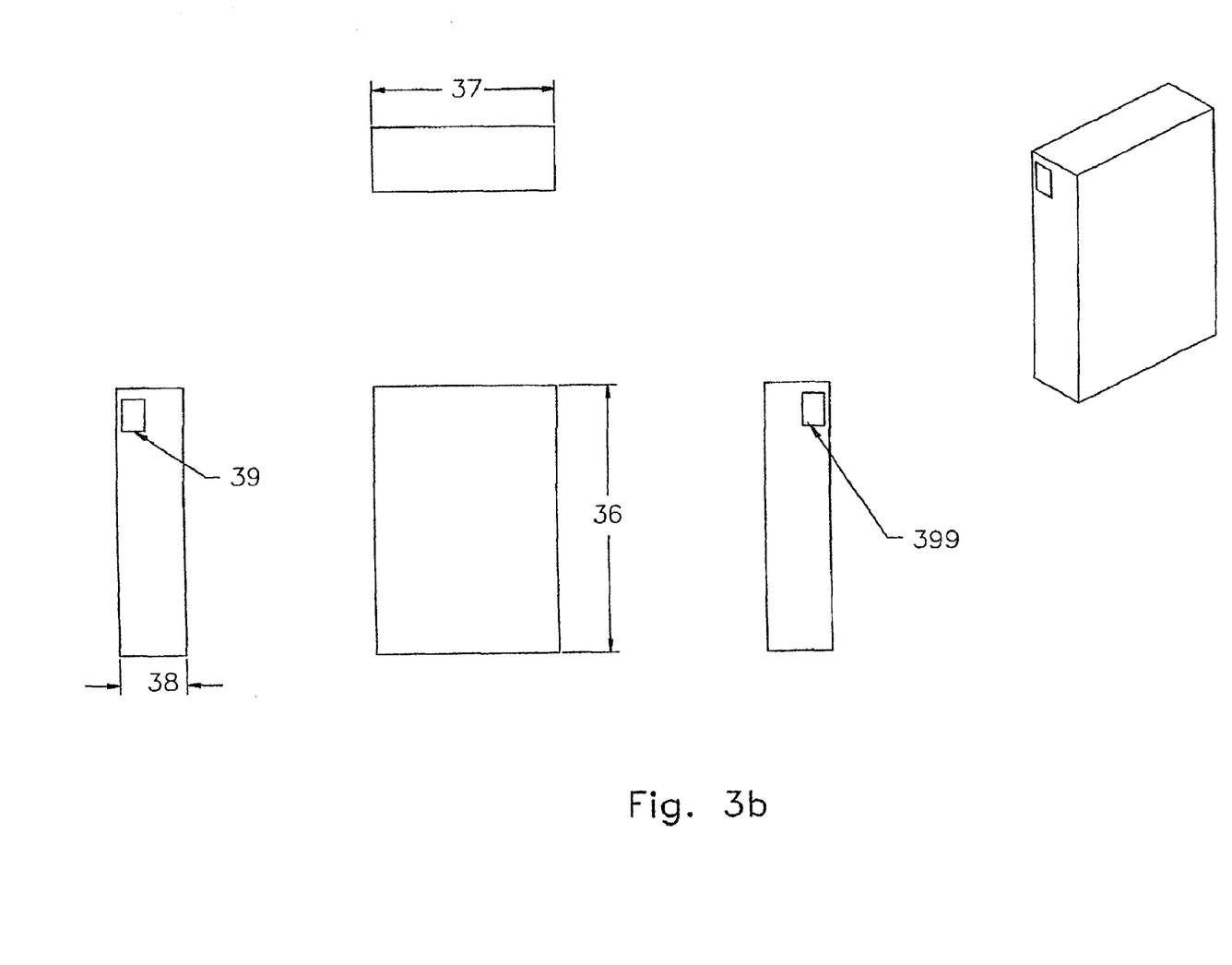
FIG. 3b similarly shows an additional range of dimensions of a zinc-air battery for use in cochlear implant systems.

An embodiment shown in FIG. 2a uses small holes (21) in a rigid case (22) to enable and facilitate the diffusive transport of air to the zinc-air battery unit in sufficient quantity. The sufficient quantity is such that a zinc-air battery of the sizes (32), (36), shown in FIGS. 3a and 3b, operates in the required power flow range. The quantitative sizes are discussed in the third paragraph below, in conjunction with FIG. 3a and FIG. 3b.

Figures 2B, 2C:
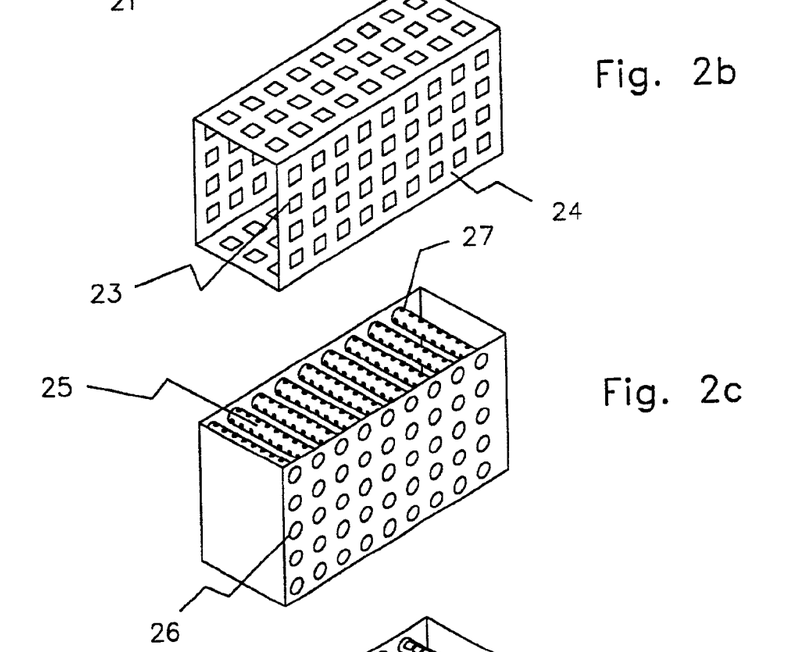
FIG. 2b shows a permeable casing made from a permeable material which covers the holes.
FIG. 2c shows a permeable casing having internal air-ducts with small holes.
Figure 2D:
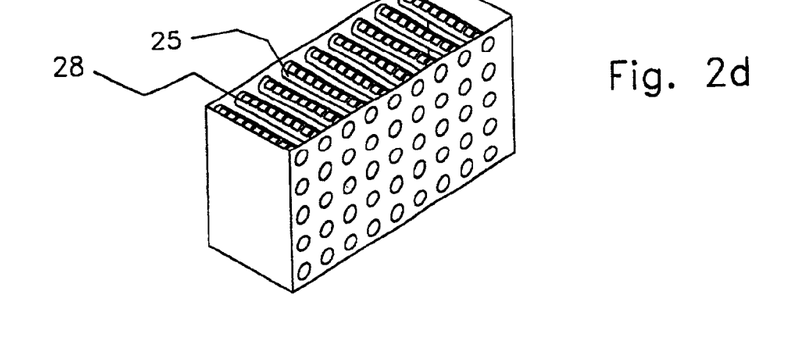
FIG. 2d shows another type of permeable casing utilizing internal air-ducts with permeable material.

Another embodiment (FIG. 2b) uses a permeable membrane (24) supported by a rigid frame or case with a case with areas cut out (23). Another embodiment (FIG. 2c) shows small pipes (25) connected through the case (26) to the outside air. These small pipes (25) have small holes (27) where the pipes are internal to the battery in order to enable the air to diffuse to more places internal to the battery case (26). Another embodiment (FIG. 2d) uses permeable membrane(s) (28) over open areas in the small pipes (25) to enable the air transport.

In all embodiments of this invention, care is taken to prevent the electrolyte, typically corrosive, such as ammonium chloride, potassium hydroxide, or neutral manganese chloride, from leaking out. Any leakage of the corrosive electrolyte could potentially harm the patient. Therefore, typically, many small, laser-drilled holes are used, which acting together with the surface tension of the electrolyte and a hydrophobic coating material such as carbon black is used to prevent electrolyte escape. Another embodiment utilizes a membrane such as tetrafluoroethylene (DuPont TEFLON) to allow the entry of air, but prevent the escape of the electrolyte.

One embodiment (FIG. 3b) of the invention is a rectangular solid shape with dimensions 6 mm (±20%) thick (38) by 25 mm (±20%) long (36) by 17 mm (±20%) wide (37), such that it can fit slidingly into a behind-the-ear (BTE) external speech-processing component of a cochlear implant. An example of an implantable cochlear stimulator is described in U.S. Pat. No. 5,603,726, which is hereby incorporated by reference. An example of a type of BTE is described in U.S. Pat. No. 5,824,022, that is hereby incorporated by reference. The positive (39) and negative (399) terminals are shown. Another embodiment (FIG. 3a) of the invention is a rectangular solid shape with dimensions 6 mm (±20%) (31) thick by 20 mm (±20%) long (32) by 10 mm (±20%) wide (33). The positive (34) and negative (35) terminals are shown. Many cochlear implants use belt-mounted batteries and speech processors. The new high-density energy source allows these latter to be dispensed with and replaced by a lightweight behind-the-ear (BTE) unit.

Figure 5A:
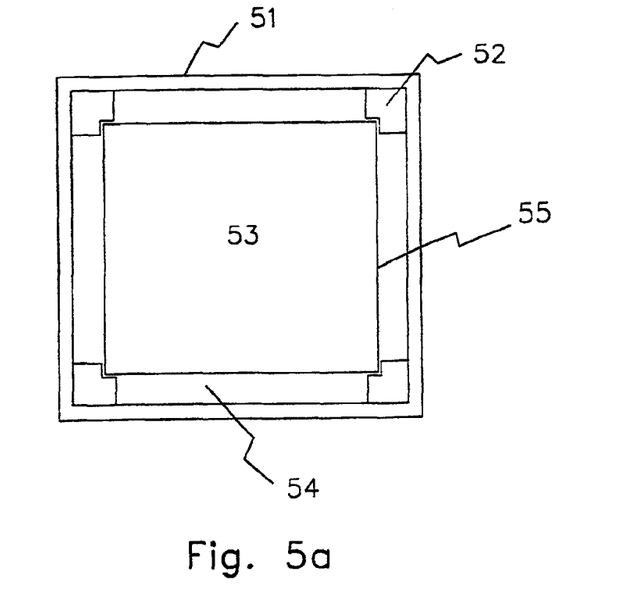
FIG. 5a illustrates details of a cochlear implant system BTE unit battery holder, showing standoffs that aid in the air circulation to the battery and its permeable case.
Figure 5B:
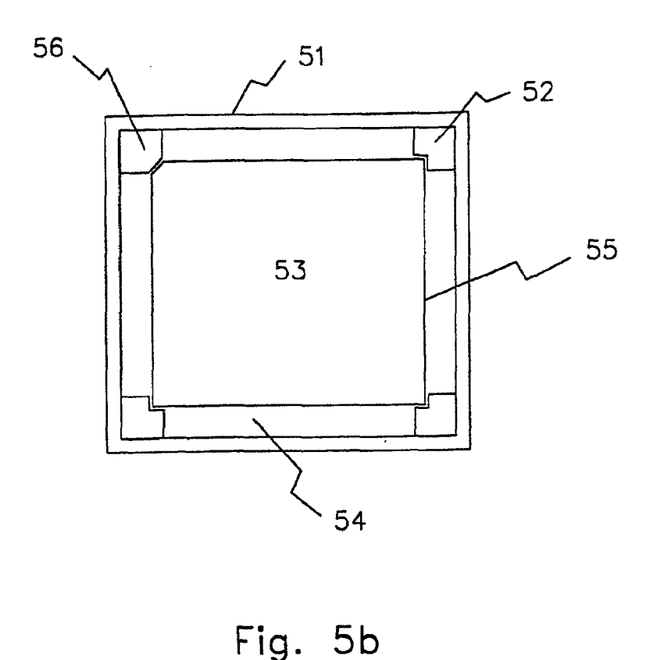
FIG. 5b similarly shows the details of a cochlear implant system BTE unit battery holder, with keyed standoffs that aid in the air circulation to the battery.
Figure 5C:
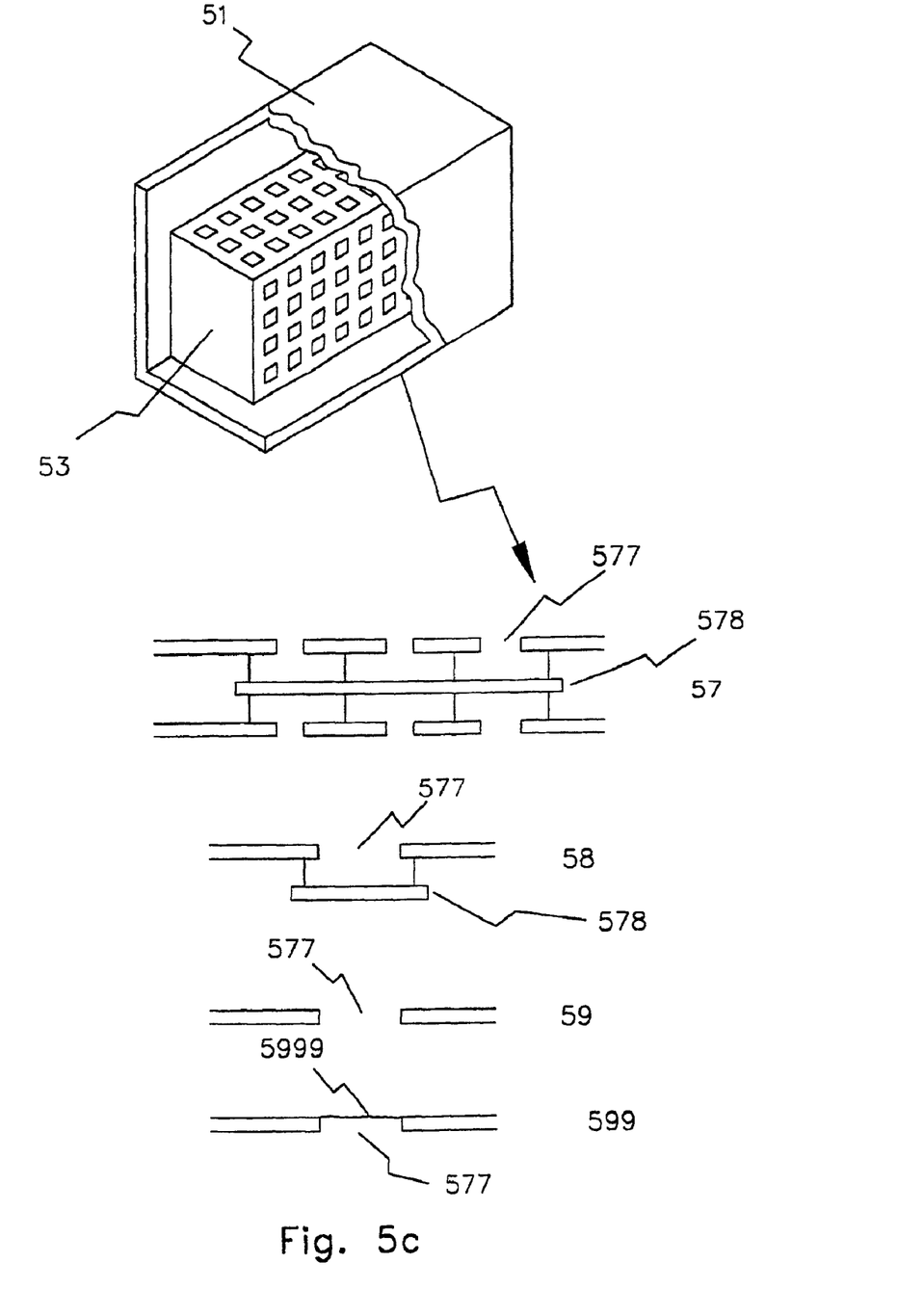
FIG. 5c depicts details of a permeable surface battery holder for use with the cochlear implant system BTE unit that aids in the air circulation to the battery.

FIG. 5a shows details of how the battery and its case are situated in the BTE cochlear implant system battery receptacle. The BTE battery holder (51) uses stand-offs (52) to allow the zinc-air battery (53) to be surrounded by air spaces (54). These air spaces allow the permeable surface (55) of the zinc-air battery (53) to have a sufficient air supply. A similar case is shown in FIG. 5b, except that here one or more standoffs (56) are keyed so as to place the positive and negative terminals of the zinc-air battery (53) correctly. FIG. 5c shows another embodiment of the BTE battery receiving housing (51) for providing air access to the zinc-air battery (53). Different surface structures such as (57) with perforations on the inner and outer layer of the BTE battery receiving housing, with a baffle unit (578), structure (58) with perforation (577) and baffle unit (578), structure (59) with perforation (577), and structure (599) with perforation (577) and permeable membrane (5999).

The zinc-air batteries typically have, in the uses cited, a flat electrode geometry. In that case, the air holes and air tube ducts are arranged so as to lead oxygen (in the air) to the air electrode and to return the air which is slightly depleted in oxygen after reacting with the zinc via the battery electrolyte. In another embodiment, the electrode pairs may be cylindrical or piecewise planar. In these cases, the air holes and/or ducts are arranged to maximize the transport of air to and from the air electrode.

A further embodiment utilizes the small tubes and tubules as mechanical elements to help prevent the desiccation in a dry ambient condition (approximately, below 40% relative humidity).

Similarly the same mechanical structure is used to help prevent "flooding" of the electrolyte, too much water in the electrolyte when the ambient conditions have high humidity (approximately, above 60% relative humidity).

The permeable membrane embodiments also may act to prevent desiccation and flooding, as well as to prevent carbon dioxide and other contaminants, such as tobacco smoke from entering the battery and decreasing its efficiency.

Figure 4:
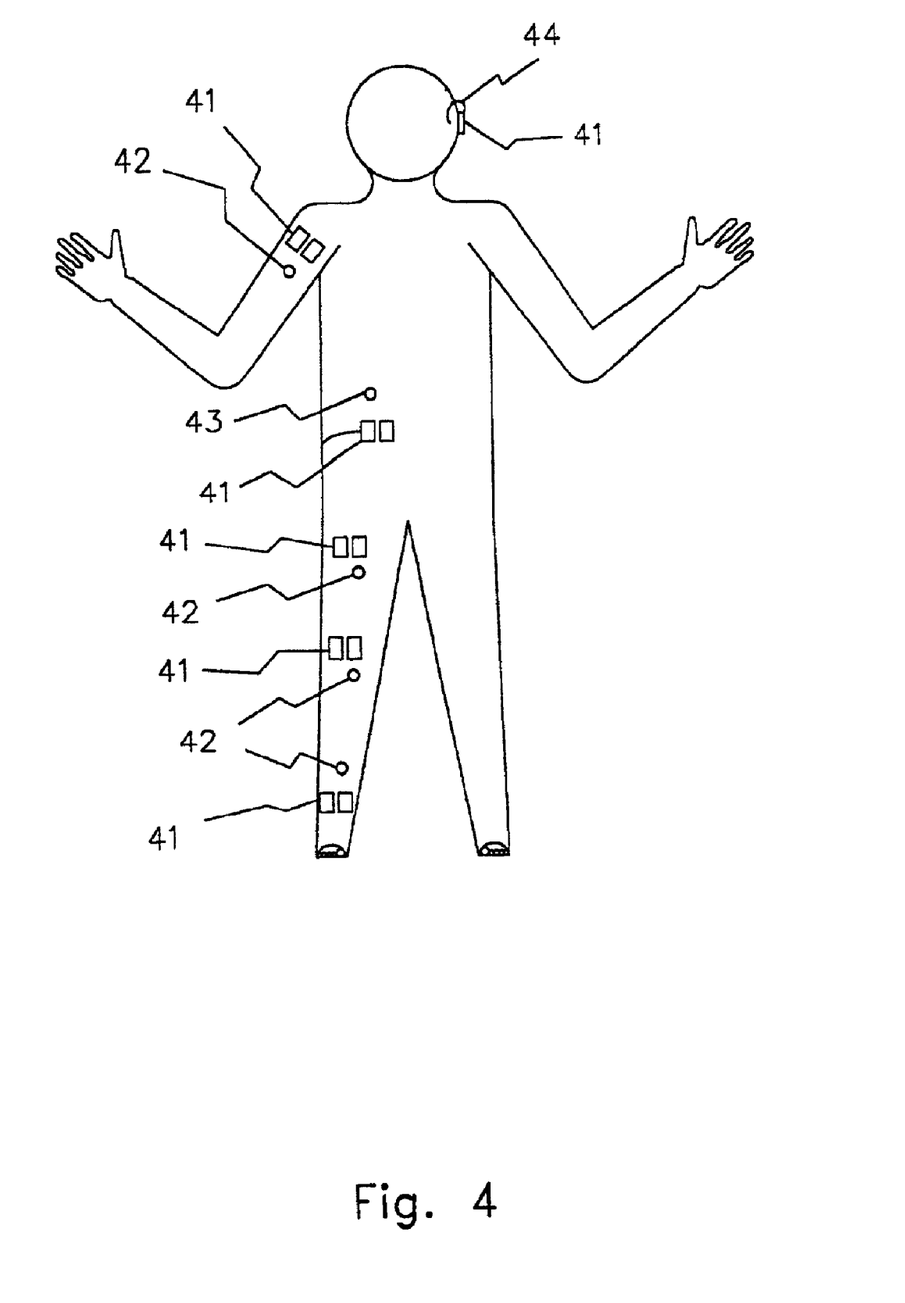
FIG. 4 depicts several lightweight, high energy density disposable primary battery systems for powering neural stimulators, muscle stimulators, neuromuscular stimulators and living tissue stimulators.

The invention is a method as well as an apparatus for increasing the air flow to a zinc-air battery such that the energy density, approximately, is from 500 mwh/cc to 1000 mwh/cc allowing about 8 to 16 hours use as a primary (throw-away) battery. It is designed for and is particularly good for use with, for example high-duty cycle, high-drain cochlear implants, and neuromuscular stimulators for nerves, muscles, and both nerves and muscles together. FIG. 4 shows various uses of the present invention. Zinc-air battery (ies) (41) may enable limb movement and locomotion via neuromuscular stimulators (42), spinal column stimulators (43), and may allow more effective use of the BTE component of cochlear implant systems (44).

The systems incorporating the high energy density energy source are also part of the invention, as well as the resulting apparatus of the method. The uses of this inexpensive, (i.e., approximately a cost of one dollar per day), throw-away primary battery are new uses of the modified zinc-air battery and are directed toward helping people hear again, walk again, and regain body functionality which they have otherwise lost permanently.

It is noted that while zinc-air batteries may be obtained commercially from numerous sources, e.g., Electric Fuel, Ltd., Har Hotzvina Science Park, P.O.B. 23073, Jerusalem, 91230, Israel, the present invention is not directed to zinc-air batteries per se. Rather, the invention is directed to zinc-air systems that include a zinc-air battery in a small, prismatic shaped case that allows sufficient air to enter the battery case so that a high power output is achieved, at low cost.

While the invention herein disclosed has been described by means of specific embodiments and applications thereof numerous modifications and variations could be made thereto by those skilled in the art without departing from the scope of the invention set forth in the claims.

What is claimed is:

1. A system for stimulating at least one neural pathway within a patient's body, wherein said system comprises:
   a first power consuming circuitry portion suitable for implantation within a patient's body, wherein said first power consuming circuitry portion is coupled to at least one neural pathway within the patient's body and said first power consuming circuitry portion is responsive to externally provided control information;
   a second power consuming circuitry portion adapted to be externally carried by the patient, wherein said second power consuming circuitry portion periodically provides said control information to said first power consuming circuitry portion;
   a zinc-air battery contained within a prismatic-shaped housing, said zinc-air battery comprising a primary power source for said second power consuming circuitry portion, wherein said primary power source has an energy density within the range of 500 mwh/cc to 1000 mwh/cc;
   means for allowing air flow through said prismatic-shaped housing of said zinc-air battery;
   an external casing for containing said second power consuming circuitry portion and said zinc-air battery within said prismatic-shaped housing; and wherein
   said casing and said prismatic-shaped housing include means for slidably coupling said prismatic-shaped housing to said casing and means for slidably decoupling said prismatic-shaped housing from said casing to enable disposal of said zinc-air battery when its stored energy has been depleted.

2. The system of claim 1 wherein:
   said system comprises a cochlear stimulation system; and
   said first power consuming circuitry portion is configured for stimulation of neural pathways in the cochlear of the patient.

3. The system of claim 2 wherein said external casing is configured to be worn behind the ear of the patient.

4. The system of claim 1 wherein said prismatic-shaped housing of said zinc-air battery comprises a rectangular-shaped housing.

5. The system of claim 4 wherein said rectangular-shaped housing of said zinc-air battery has dimensions of 6–8 mm thick by 20–25 mm long by 10–17 mm wide.

6. The system of claim 1 wherein:
   said means for slidably coupling said prismatic-shaped housing to said external casing comprise a battery holder on said external casing; and wherein
   one edge of said battery housing is adapted to slide into said battery holder.

7. The system of claim 1 wherein:
   said means for slidably coupling said prismatic-shaped housing to said external casing comprises a battery holder;
   said means for allowing air flow through said prismatic-shaped housing of said zinc-air battery comprises stand-offs that allow said zinc-air battery to be surrounded by air spaces; and wherein
   said zinc-air battery has a permeable surface through which air flows.

8. The system of claim 1 wherein said means for allowing air flow through said prismatic-shaped housing of said zinc-air battery comprises air holes in the sides of said prismatic-shaped housing.

9. The system of claim 1 wherein said means for allowing air flow through said prismatic-shaped housing of said zinc-air battery comprises at least one side of said prismatic-shaped housing being made from a permeable membrane.

10. The system of claim 1 wherein said means for allowing air flow through said prismatic-shaped housing comprised air pipes connected through said housing to outside air, said air pipes having holes therein where said pipes are internal to said housing.

11. The system of claim 10 wherein said means for allowing air flow through said prismatic-shaped housing comprises air pipes connected through said housing to outside air, said air pipes having open areas therein where said pipes are internal to said housing; and wherein said open areas are covered with an air-permeable membrane to enable air transport therethrough.

12. The system of claim 1 wherein:

said system comprises a muscular stimulation system for causing a muscle to contract; and said first power consuming circuitry portion is configured for stimulation of a neural pathway that causes a muscular contraction in the patient.

13. The system of claim 1 wherein:

said system comprises a muscular stimulation system for causing a muscle to contract; and said first power consuming circuitry portion is configured for directly stimulating a muscle in the patient.

14. The system of claim 1 wherein said second power consuming circuitry portion additional provides operating power to said first power consuming circuitry portion.

15. A system for stimulating tissue within a patient's body, wherein said system comprises:

a biological tissue stimulator having at least a portion of its circuitry adapted to be externally carried by the patient;

a zinc-air battery contained within a prismatic-shaped housing, said zinc-air battery comprising a primary power source for said externally carried circuitry portion, wherein said primary power source has an energy density within the range of 500 mwh/cc to 1000 mwh/cc;

means for allowing air flow through said prismatic-shaped housing of said zinc-air battery;

an external casing for containing said circuitry portion and said zinc-air battery within said prismatic-shaped housing; and wherein said casing and said prismatic-shaped housing include means for slidably coupling said prismatic-shaped housing to said casing and means for slidably decoupling said prismatic-shaped housing from said casing to enable disposal of said zinc-air battery when its stored energy has been depleted.

16. The system of claim 15 wherein said biological tissue stimulator comprises a cochlear stimulation system.

17. The system of claim 15 wherein said biological tissue stimulator comprises a cochlear stimulator system and wherein said cochlear stimulator system comprises:

a first power consuming circuitry portion suitable for implantation within a patient's body, wherein said first power consuming circuitry portion is coupled to at least one neural pathway within the patient's body and said first power consuming circuitry portion is responsive to externally provided control information;

a second power consuming circuitry portion adapted to be externally carried by the patient, wherein said second power consuming circuitry portion periodically provides said control information to said first power consuming circuitry portion.

18. The system of claim 15 wherein said external casing is configured to be worn behind the ear of the patient.

19. The system of claim 15 wherein said prismatic-shaped housing of said zinc-air battery comprises a rectangular-shaped housing.

20. The system of claim 19 wherein said rectangular-shaped housing of said zinc-air battery has dimensions of 6–8 mm thick by 20–25 mm long by 10–17 mm wide.

* * * * *

UNITED STATES PATENT AND TRADEMARK OFFICE
CERTIFICATE OF CORRECTION

PATENT NO. : 6,879,855 B2
DATED : April 12, 2005
INVENTOR(S) : Schulman et al.

It is certified that error appears in the above-identified patent and that said Letters Patent is hereby corrected as shown below:

<u>Column 6,</u>
Line 31, to read as follows:
-- for stimulation of neural pathways in the cochlea of --
Line 43, to read as follows:
-- housing to said external casing comprises a battery --

<u>Column 7,</u>
Line 1 to read as follows:
-- comprises air pipes connected through said housing to --

<u>Column 8,</u>
Line 21 to read as follows:
-- externally provided control information; and --

Signed and Sealed this

Seventh Day of June, 2005

JON W. DUDAS
*Director of the United States Patent and Trademark Office*